(12) United States Patent
Culbert (10) Patent No.: US 7,282,728 B2
(45) Date of Patent: Oct. 16, 2007

(54) MODULAR FIXTURE

(75) Inventor: Robert Culbert, Manhattan Beach, CA (US)

(73) Assignee: Steril-Aire, Inc., Burbank, CA (US)

( * ) Notice: Subject to any disclaimer, the term of this patent is extended or adjusted under 35 U.S.C. 154(b) by 216 days.

(21) Appl. No.: 10/934,811

(22) Filed: Sep. 3, 2004

(65) Prior Publication Data

US 2006/0049368 A1    Mar. 9, 2006

(51) Int. Cl.
*A61N 5/06* (2006.01)
*G01J 3/10* (2006.01)
*H05G 2/00* (2006.01)

(52) U.S. Cl. .................. 250/504 R; 362/219; 362/222

(58) Field of Classification Search ............ 250/504 R, 250/432 R, 435, 436; 362/225, 230
See application file for complete search history.

(56) References Cited

U.S. PATENT DOCUMENTS

| 5,550,725 | A |  | 8/1996 | Shemitz |  |
| 5,558,158 | A |  | 9/1996 | Elmore |  |
| 5,742,063 | A |  | 4/1998 | Scroggins |  |
| 5,902,552 | A |  | 5/1999 | Brickley |  |
| 6,634,772 | B2 |  | 10/2003 | Yaphe |  |
| 6,670,626 | B2 | * | 12/2003 | Witham et al. | 250/504 R |

\* cited by examiner

*Primary Examiner*—David A. Vanore
(74) *Attorney, Agent, or Firm*—SoCal IP Law Group LLP; Steven C. Sereboff; John E. Gunther (57) ABSTRACT

There is disclosed an electric discharge lamp fixture and a process of assembling a modular germicidal system. The electric discharge lamp fixture may be attached to and receive substantial mechanical support solely from at least one other electric discharge lamp fixture. The process of assembling the modular germicidal system may comprise electrically connecting an electric discharge lamp fixture to an other electric discharge lamp fixture, wherein connecting the electric discharge lamp fixture to the other electric discharge lamp fixture aligns the electric discharge lamp fixture for mounting to the other electric discharge lamp fixture. The process of assembling the modular germicidal system may comprise mounting the electric discharge lamp fixture to the other electric discharge lamp fixture, wherein the electric discharge lamp fixture receives substantial mechanical support solely from at least the other electric discharge lamp fixture.

24 Claims, 4 Drawing Sheets

MODULAR FIXTURE

NOTICE OF COPYRIGHTS AND TRADE DRESS

A porton of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

BACKGROUND OF THE INVENTION

1. Field of the Invention

The present invention relates to lamp fixtures.

2. Description of the Related Art

Many businesses, offices, and homes utilize modular lighting systems. A modular lighting system is a sequentially joined and electrically connected plurality of lamp modules. A lamp module is a fixture supporting and powering a lamp, wherein the lamp module has a standardized form to interlock and electrically connect with other lamp modules, couplers, and junctions.

Lamp modules, in general, are individually mounted to walls, ceilings, tracks, and suspension systems. A suspension system is a system for hanging the lamp modules from a mechanical structure such as an I-beam or rafter. Suspension systems typically include rods, chains, or wires for hanging the lamp modules.

Conference rooms typically utilize alcove mounted modular lighting systems to provide indirect lighting. Factories typically utilize continuous row suspended modular lighting systems to provide direct overhead lighting. Commercial buildings typically utilize wall mounted modular lighting systems to provide wall wash deco lighting. Retail stores typically utilize modular lighting systems to provide lighting within display cases.

DETAILED DESCRIPTION OF THE INVENTION

Throughout this description, the embodiments and examples shown should be considered as exemplars, rather than limitations on the apparatus and methods of the present invention.

Figure 1:
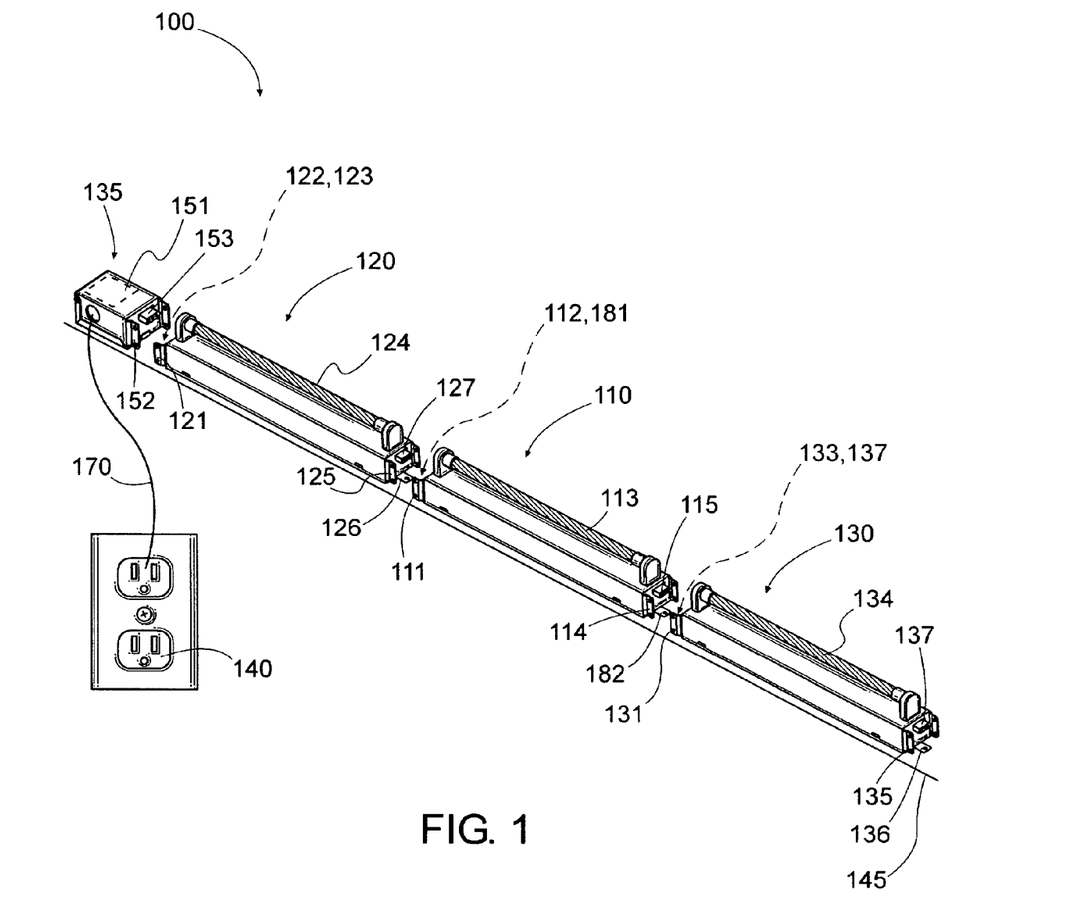
FIG. 1 is a exploded perspective view of a modular emitter system.

Referring now to FIG. 1, there is shown an exploded perspective view of a modular emitter system 100. The modular emitter system 100 may include a first lamp fixture 110, a second lamp fixture 120, a third lamp fixture 130, a junction box 135, a power source 140, and a wall 145. The modular emitter system 100 may be installed in an office building, a conference room, an air duct of a heating, ventilation and air conditioning (HVAC) system, a mass transit vehicle, a food storage and/or handling room, or other area.

Figure 2:
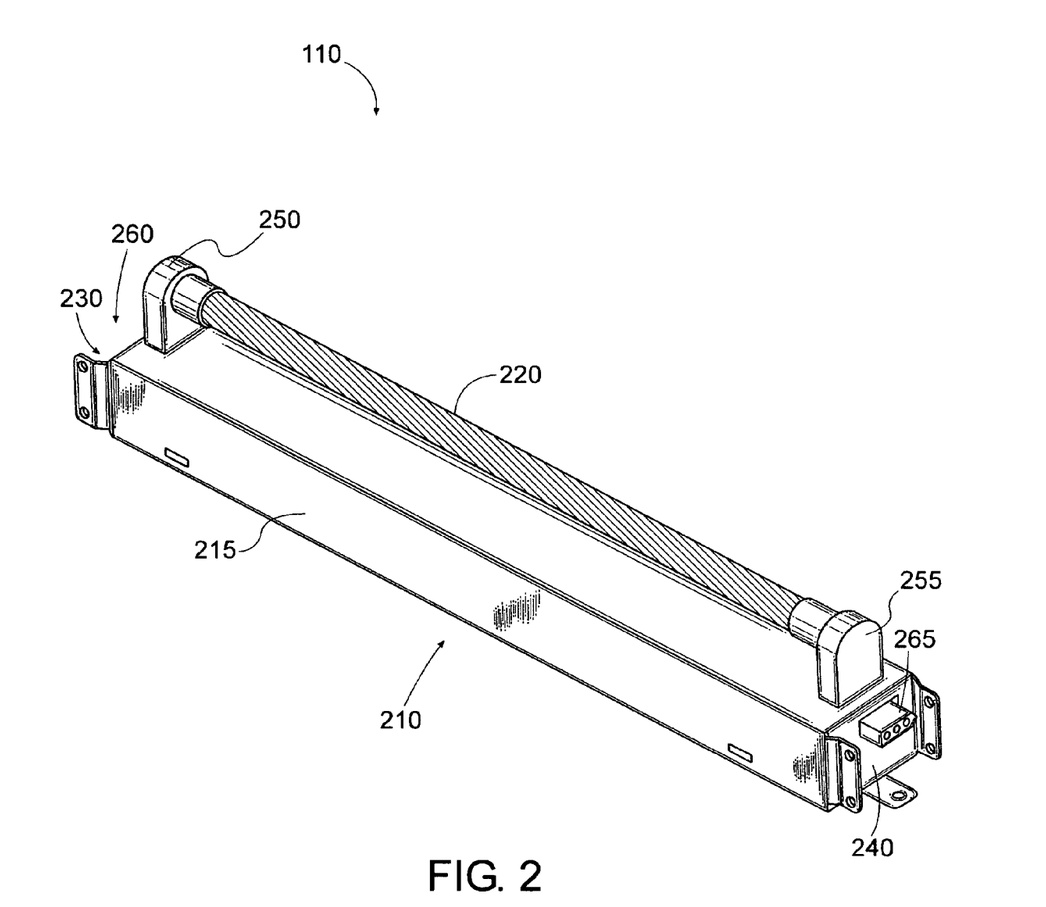
FIG. 2 is a perspective view of a lamp module.

Referring now to FIG. 2, there is shown a perspective view of the first lamp fixture 110. The first lamp fixture 110 may include a fixture 210 and a lamp 220.

The lamp 220 may be an electric discharge lamp or other type of lamp. The term electric discharge lamp refers to an apparatus which emits radiation caused by an electric discharge from electrodes in an enclosure. An electric discharge is electrical conduction through a gas or vapor in an applied electric field. An enclosure is a hollow device used to hold vaporizable materials and gases. An enclosure may be at least partially translucent. An enclosure may be constructed of glass, metal, quartz, or plastic. Electric discharge lamps may be fluorescent lamps, mercury vapor lamps, low pressure sodium lamps and high pressure sodium lamps. If the lamp 220 is an electric discharge lamp, then the lamp fixture 110 is referred to as an electric discharge lamp fixture.

The lamp 220 may include a vaporizable material, such as mercury. The mercury, when electrically excited, may emit ultraviolet light at a germicidal wavelength. A germicidal wavelength may be at an ultraviolet-C (UVC) wavelength. A germicidal wavelength, for example 187 nm and 254 nm, is a wavelength of light which retards buildup or accumulation of undesirable substances. Undesirable substances may include at least one of mold, bacteria, fungi, viruses, mildew, allergens, spores, yeasts, mycotoxins, and endotoxins.

When the modular emitter system 100 is installed and operating, the lamp 220 may emit UVC radiation within an air duct (not shown) and to a drain pan (not shown) of an HVAC system (not shown). The HVAC system may provide conditioned air to a room. The room may be occupied by people and/or animals. Because the lamp 220 may emit UVC, the lamp 220 may at least partially sterilize the air provided to the room. If the lamp 220 at least partially sterilizes the air provided by the HVAC system, the indoor air quality (IAQ) of the room may be improved.

When the modular emitter system 100 is installed and operating, the lamp 220 may emit UVC radiation to food processing systems. Food processing systems refer to any automated or partially automated food handling, preparing, packaging, cooking, mixing, baking, and similar systems. Food processing systems may package or otherwise place food in a container for delivery to a point of further distribution and eventual sale. The UVC radiation may treat the food processing machinery and remove some of the potentially harmful germs, bacteria, other contaminants and the like from the food processing systems and the air surrounding the food processing systems.

The fixture 210 may provide mechanical support and electrical power to the lamp 220. The fixture 210 may be a modular fixture. The term modular fixture refers to a fixture having a standardized form to mechanically or otherwise interlock and electrically connect with other fixtures, couplers, and junctions. Modular fixtures may be installed in a variety of combinations. Different length modular fixtures, T-junctions, metal flex conduit, and couplers may be configured to expose the components of an HVAC system to UVC radiation.

The fixture 210 may include a housing 215, a first socket 250, a second socket 255, a first connector 260, and a second connector 265. The housing 215 may include a first end 230 and a second end 240. An housing is a structure which provides support to mechanical components and at least partially encloses electrical components. Mechanical components may include a socket, a connector, and a lamp. Electrical components may include wiring.

The housing 215 may have an elongate structure with a square, rectangular, oval, teardrop, or other shaped cross section. For example purposes, the housing 215 of FIG. 2 may have a rectangular cross section having dimensions of approximately 1.8"×1.9" or other dimensions. Common housings are manufactured in lengths of approximately 18", 24", 30", 36", 42" and other lengths. The housing 215 may be manufactured from a single piece of material or multiple components that are fastened, welded, magnetically attached, or attached by another method.

The housing 215 may be manufactured from a metal, a composite fiber, a plastic, or other material. The material of the housing 215 may be selected based on requirements for bending and torsional rigidity. For example, if the housing 215 receives mechanical support only at the first end 230 and the second end 240, an aluminum, steel, or other rigid material may be selected. If the housing 215 provides rigidity to the first lamp fixture 110, the modular emitter system 100 may not require a structural spine, backbone, or track to provide rigidity to the first lamp fixture 110. Typical structural spines, backbones, and tracks have a length dimension of at least two meters. Structural spines, backbones, and tracks with a length of several meters may be difficult and expensive to ship. If structural spines, backbones, and tracks may be omitted from the modular emitter system 100, shipping and logistics cost savings may be achieved.

The first socket 250 and the second socket 255 may be attached to the housing 215. The relative position of the first socket 250 to the second socket 255 may be selected based on the length and type of the lamp 220. Common electric discharge lamps are manufactured in lengths of approximately 16", 22", 28", 34", 40", and other lengths. The first socket 250 and second socket 255 may have an industry standard form such as a bi-pin, a single pin, a R17d, a medium bi-pin, a four pin, a 2Gx13, a recessed double contact, a G-23, or a 2G-11. The first socket 250 and second socket 255 may receive mechanical support from the housing 215. The first socket 250 and second socket 255 may provide mechanical support and electric power to the lamp 220.

Figure 3:
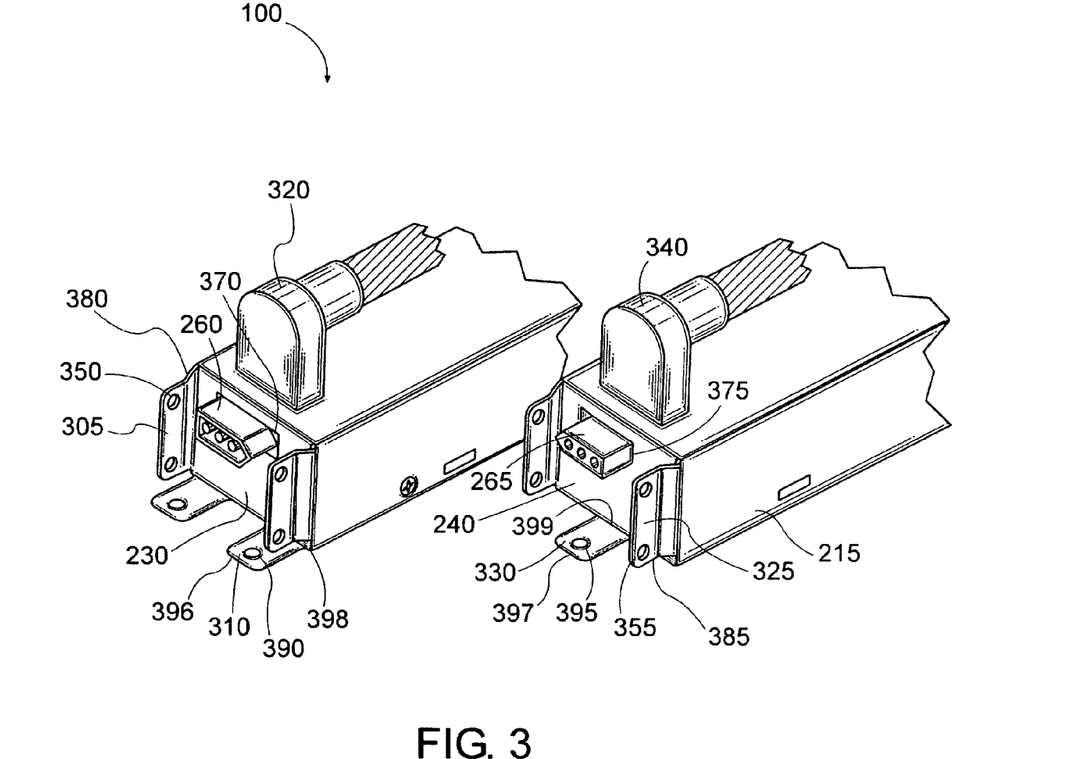
FIG. 3 is a partial cut away view of the ends of a lamp module.

Referring now to FIG. 3, there is shown a perspective view of the first end 230 and the second end 240 of the first lamp fixture 110 of FIG. 2. The first end 230 may include a first opening 370. The second end 240 may include a second opening 375. The dimensions, geometry, and location of the first opening 370 and the second opening 375 may be selected to allow the respective first connector 260 and second connector 265 to pass through, or be disposed within or behind the respective first and second opening 370, 375. The first opening 370 and the second opening 375 may have a rectangular, circular, or other shape. The first opening 370 and the second opening 375 may have dimensions of approximately 1" in width and approximately 0.36" in height. The location of the first opening 370 relative to the first end 230 may be selected to be the mirror image of the location of the second opening 375 relative to the second end 240. Thus, when the first connector 260 of the first lamp fixture 110 is connected to the second connector 265 of another lamp fixture, the first lamp fixture 110 and the another lamp fixture may be inline and symmetrical relative to each other.

The first connector 260 and the second connector 265 may be respectively attached to and receive mechanical support from the first end 230 and the second end 240. The first connector 260 and the second connector 265 may be attached to and receive mechanical support from the housing 215. The first connector 260 and the second connector 265 may respectively be at least partially disposed within the first opening 370 of the first end 230 and the second opening 375 of the second end 240.

The first connector 260 and the second connector 265 may respectively protrude out of the housing 215 in the respective direction that the first end 260 and the second end 265 faces. The first connector 260 and the second connector 265 may be at least partially recessed within the housing 215. The first and/or second connector 260, 265 may be at least partially disposed within the housing 215 so that when the first lamp fixture 110 is attached to another lamp fixture, the first end 230 may be flush with the second end 240.

The first connector 260 and the second connector 265 may have an industry or commercially standard form such as a push together connector, a snap together connector, a plug and socket type connector, or other type of connector. The first connector 260 and the second connector 265 may have a male form, a female form, or a unisex form. The first connector 260 and the second connector 265 may be electrically connected to each other via electrical wiring (not shown) within the housing 215. The first connector 260 and the second connector 265 may be electrically connected to the first socket 250 and the second socket 255 via electrical wiring (not shown) within the housing 215.

The first lamp fixture 110 may be manufactured with the electrical wiring installed within the housing 215. The first lamp fixture 110 may ship from the manufacturer's factory pre-wired. Typically, installers of modular emitter systems must wire each lamp fixture to electrically connect the sockets and connectors. If the installer of the modular emitter system 100 receives each lamp fixture as a pre-wired unit, installation costs may be saved and potential errors in wiring may be reduced. If wiring errors are minimized, risk of fire, electric shorting, electrical shocks, and/or electrocution maybe avoided.

The first end 230 may include a first modular flange 305, and a first mounting flange 310. The second end 240 may include a second modular flange 325, and a second mounting flange 330.

A flange is a surface for attaching one body to another. The term modular flange refers to a flange of a modular fixture, coupler or junction, wherein the modular flange has a standardized form to attach to other modular flanges of other modular fixtures, couplers and junctions. The first modular flange 305 may be a single flange extending from the housing 215 beyond the first end 230 in the direction that the first end 230 faces. The first modular flange 305 may be two or more flanges wherein the flanges extend from adjacent or opposite surfaces of the housing 215. For example purposes, the first modular flange 305 may include two flanges extending from opposite surfaces of the housing 215. If a lamp fixture is attached to another lamp fixture via a first modular flange 305 having two flanges, the attachment may provide more torsional rigidity than if the first modular flange 305 has only one flange.

The second modular flange 325 may extend from the housing 215 beyond the second end 240 in the direction that the second end 240 faces. The second modular flange 325 may be a single flange or a plurality of flanges.

The geometry of the first modular flange 305 and the second modular flange 325 may be rectangular, round, or other shape. The geometry of the first modular flange 305 and the second modular flange 325 may be selected so that when the first connector 260 of the first lamp fixture 110 is connected to the second connector 265 of the another lamp fixture, the first modular flange 305 of the first lamp fixture 110 is aligned for attachment to the second modular flange 325 of the another lamp fixture. The first modular flange 305 and the second modular flange 325 may have dimensions of approximately 0.555" in length and approximately 1.53" in height, or other dimensions.

The first modular flange 305 and the second modular flange 325 may respectively include a first bend 380 and a second bend 385. The first bend 380 and the second bend 385 may offset the first modular flange 305 and the second modular flange 325 from a plane where a surface of the housing 215 is within. The offset for the first bend 380 and the second bend 385 may be in an inward direction. If the offset is in an inward direction, the first bend 380 and the second bend 385 will not protrude beyond the plane where the surface of the houseing 215 is within. Thus, the lamp fixtures may be mounted sequentially and flush against another surface.

For example purposes, the first modular flange 305 and the second modular flange 325 may be offset from a plane where a surface of the housing is within by approximately 0.1" and 0.2", respectively, or other dimensions. The first bend 380 and the second bend 385 may include different offset dimensions. When the first connector 260 of the first lamp fixture 110 is connected to the second connector 265 of another lamp fixture, the first modular flange 305 may be disposed alongside the second modular flange 325.

The first modular flange 305 may define an opening 350. The opening 350 may include dimensions, geometry and location to allow a fastener (not shown) to pass through. The opening 350 of the first modular flange 305 may be a single opening or a plurality of openings. The opening 350 of the first modular flange 305 may have a circular, triangular or other shape. For example purposes, the opening 350 of the first modular flange 305 may be two circular holes per flange, disposed symmetrically relative to each flange, having a center to center distance of approximately 1.178" and a diameter of approximately 0.2", or other dimensions.

The second modular flange 325 may define an opening 355. The opening 355 may include a single opening or a plurality of openings. The opening 355 may be based on the opening 350 of the first modular flange 305.

The fastener may be installed through the opening 350 of the first modular flange 305 of the first lamp fixture 110 and the opening 355 of the second modular flange 325 of the another lamp fixture. The fastener may be integrated with the first modular flange 305 of the first lamp fixture 110 and the second modular flange 325 of the another lamp fixture.

The first lamp fixture 110 may be attached to another lamp fixture via the first modular flange 305, the housing 215, the socket 250, or any other surface or component of the first lamp fixture 110. The first lamp fixture 110 may be attached to the another lamp fixture via any attaching means. Attaching means may include magnets, adhesives, clips, clasps, latch, anchor, band, binding, hook, brace, rope, wire, tack, twine, clamps, fasteners, screws, bolts, rivets, weldings, brazings, solderings, straps, and plugs.

A mounting flange is a surface for attaching a fixture to a fixed surface or member such as a wall, a ceiling, a floor, a duct, a bracket, a track, a frame, a chain, a rope, and combinations thereof. The first lamp fixture 110 may be attached to a fixed surface or member at the first and second mounting flange 310, 330, the housing 215, the sockets 250, 255, or other surface or component of the first lamp fixture 110. The first lamp fixture 110 may be attached to the fixed surface via any attaching means.

The first and second mounting flange 310, 330 may extend from the housing 215 beyond, respectively, the first and second end 230, 240 in the direction that the first and second end 230, 240 faces. The first mounting flange 310 and the second mounting flange each may include one flange or a plurality of flanges. The disposition and number of flanges that the first mounting flange 310 and the second mounting flange 330 may include may be selected for the installer to quickly determine the electric polarity of each end of each lamp fixture.

The first mounting flange 310 and the second mounting flange 330 may be disposed in different relative positions to the first end 230 and the second end 240. For example, the first mounting flange 310 may be disposed near a corner 398 of the first end 230 and the second mounting flange 330 may be disposed near the center along an edge 399 of the second end 240. Because the first mounting flange 310 may be disposed relative to the first end 230 in a different position than the second mounting flange 330 is to the second end 240, the installer likely will not confuse which end is the first end 230 and which end is the second end 240. Moreover, the different relative positions of the first mounting flange 310 and the second mounting flange 330 to the respective first end 230 and second end 240 may help guide the installer in positioning adjacent fixtures. If the installer, in error, attempts to connect the first connector 260 of the first lamp fixture 10 with the first connector 260 of the another lamp fixture, the connectors, mounting flanges, and modular flanges may be damaged. Therefore, if confusion is minimized as to which end is which, damage to the connectors, mounting flanges, and modular flanges may be avoided.

The first mounting flange 310 and the second mounting flange 330 may include the shape of a finger, a tab, a rectangle, an oval or other shape. The geometry of the first mounting flange 310 and the second mounting flange 330 may include dimensions of 0.75" in length and 0.562" in width, or other dimensions. The first mounting flange 310 and the second mounting flange 330 may include rounded and/or beveled edges to prevent injury to an installer.

The first mounting flange 310 and the second mounting flange 330 may respectively define an opening 390, 395. The openings 390, 395 may provide a location where a fastener (not shown) may mount the first mounting flange 310 and the second mounting flange 330 to a duct of an HVAC system, a backbone, a track or other mounting surface. The dimensions, geometry, and location of the openings 390, 395 may be selected based on the dimensions of a fastener (not shown) that may support the weight of at least 1.5 lamp fixtures. For example, the openings 390, 395 may be circular with a diameter of approximately 0.2", or other dimension. The openings 390, 395 may be disposed relative to the first mounting flange 310 and second mounting flange 330 near the center of the respective first mounting flange 310 and second mounting flange 330. The openings 390, 395 may be disposed relative to the first mounting flange 310 and second mounting flange 330 approximately 0.188" or other dimension from the respective tips 396, 397 of the first mounting flange 310 and the second mounting flange 330.

Figure 4:
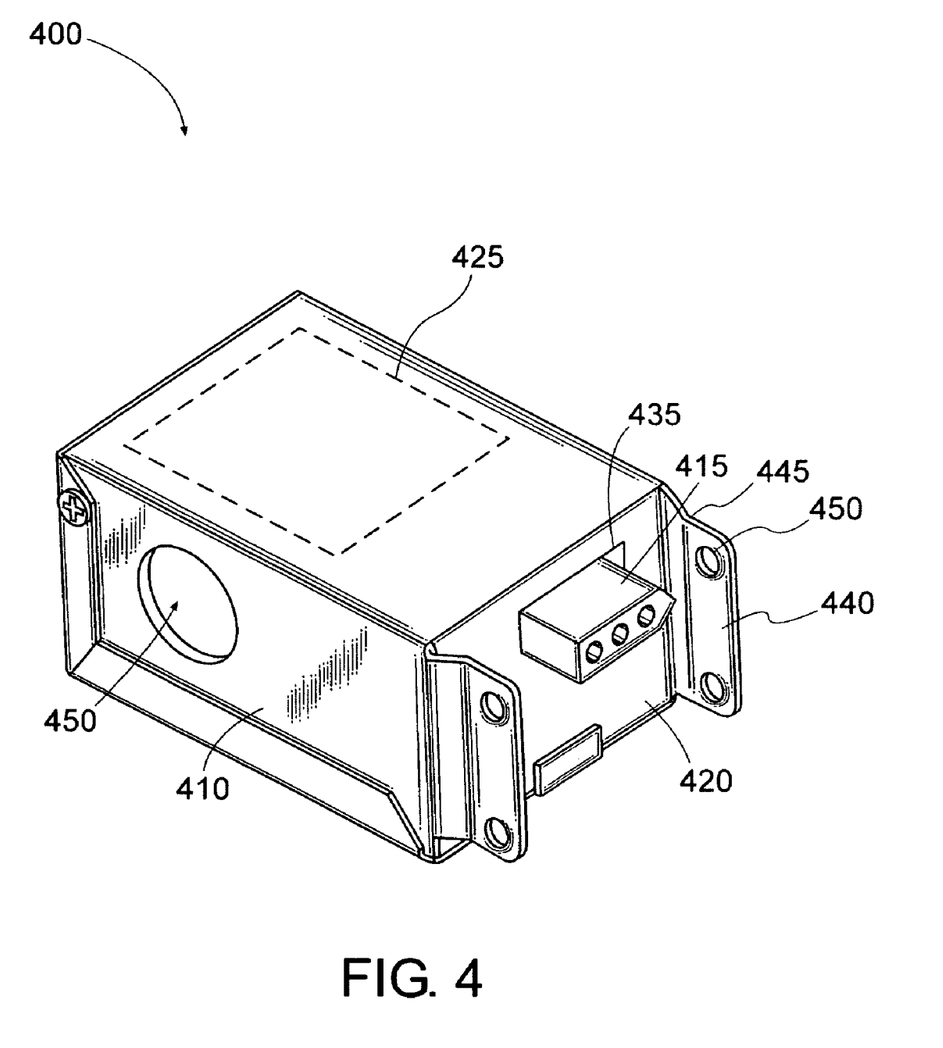
FIG. 4 is a perspective view of a junction box.

Referring now to FIG. 4, there is shown a perspective view of a junction box 400. The junction box 400 may be a module which provides power to the modular emitter system 100. The junction box 400 may include a housing 410, and a connector 415. The housing 410 may include an end 420. The housing 410 may at least partially enclose and provide mechanical support to a power supply 425.

A power supply is an electronic device or system that converts electric power from a form being received to a form which is supplied to a load. The power supply 425 may convert power from DC to AC, from DC to DC, or from AC to DC, or other. The power supply 425 may regulate electric power. The power supply 425 may be a ballast.

A ballast regulates electric power and functions as a starting and control unit for an electric discharge lamp. The ballast initially provides a voltage to ionize the gas or vaporizable material in the enclosure. The ballast then controls the power that drives the electric discharge lamp.

The power supply 425 may be selected based on the type of lamp that it may power and the desired output characteristics. The power supply 425 may include over-current protection via an inline fuse (not shown). The power supply 425 may be adjustable with regard to transforming characteristics, cycling characteristics, and capacity. The power supply 425 may be a stand-alone unit.

The term power source refers to a device or system which provides electrical power. Power sources may include one of or combinations of a battery, a solar cell, an industrial building's AC power, and a household AC power. The power source may be selected, configured or adapted based on the number of modular emitters that will be powered.

The dimensions of the housing 410 may be based on the dimensions of the power supply 425. For example purposes, the housing 410 may have dimensions of approximately 1.8" in width by 1.9" in height by 3.0" in depth, or other dimensions.

The connector 415 may be electrically connected to the power supply 425 via electrical wires (not shown).

The geometry of the modular flange 440 may be based on the geometry of the first or second modular flanges 305, 325 of the another lamp fixture.

When the connector 415 is connected to the first connector 260 or the second connector 265 of the first lamp fixture 110, the modular flange 440 may be aligned for mounting to the respective first modular flange 305 or second modular flange 325 of the first lamp fixture 110.

The modular flange 440 may define an opening 450. The opening 450 may be selected to allow a fastener (not shown) to pass through. The fastener may attach the junction box 400 to the another lamp fixture. The junction box 400 may be attached to the another lamp fixture via an adhesive, magnet, welding or other attachment method.

Referring again to FIG. 1, there is shown a modular emitter system 100 wherein the first lamp fixture 120 is attached solely to at least one other lamp fixture. The first, second, and third lamp fixtures 110, 120, 130 may include a respective first modular flange 111, 121, 131, a first connector 112, 122, 132, a lamp 113, 124, 134, a second modular flange 114, 125, 135, a second connector 115, 127, 137 a first mounting flange 181, 123, 133, and a second mounting flange 182, 126, 136.

The second and third lamp fixture 120, 130 may receive substantial mechanical support via fasteners that secure the first and second mounting flanges 123, 133, 126, 136 to the wall 145. Substantial refers to a large degree or the main part of something. Substantial mechanical support may provide for the lamp fixtures to remain stationary when the lamp fixtures are exposed to forces such as gravity, winds, vibration, and shock. The second and third lamp fixture 120, 130 may receive substantial mechanical support via an adhesive, magnet, welding or other attachment method that secures the and second mounting flanges 123, 133, 126, 136 to the wall 145.

Vibration refers to a periodic motion of a mass in alternately opposite directions from the position of equilibrium when that equilibrium has been disturbed, for example by a sinusoidal force. Vibration may be introduced to the modular emitter system 100 when, for example, a compressor of an HVAC system is operating.

Shock refers to an impact as in a striking, an impinging, or a collision. Shock, physically characterized, is the reaction of the mass to the rate of change of an applied force. Shock, may be introduced to the modular emitter system 100 when, for example, a person or a bird bumps into the wall 145.

The first lamp fixture 110 may receive substantial, principal, and/or tenacious mechanical support via the first and second modular flange 111, 114. Principal refers to the main or most important element. If the first lamp fixture 110 receives principal mechanical support via the first and second modular flange 111, 114, mechanical support received from other components or devices are not necessary for the first lamp fixture 110 to remain secured to the modular emitter system. Tenacious refers to strongly adhering to each other. Because the first lamp fixture 110 may receive substantial, principal, and/or tenacious mechanical support via the first and second modular flange 111, 114, the first and second mounting flange 181, 182 need not be attached to the wall 145.

The modular emitter system 100 may be mounted to a wall 145 wherein the wall 145 may include sections that may not accept mounting of the first lamp fixture 110. For example, a section of the wall 145 may include fiber optic or electrical wiring that may fail if a fastener is attached to that section. Additionally, a section of the wall 145 may be non-structural, very thin, or not have enough strength to support the mounting of a first lamp fixture 110. Since the first lamp fixture 110 may be mounted to adjacent lamp fixtures, the first lamp fixture 110 may be positioned over a section of the wall 145 without the first or second mounting flange 181, 182 being attached to the wall 145.

The junction box 135 may include a power supply 151, a modular flange 152, and a connector 153. The junction box 140 may receive substantial mechanical support solely from the attachment of the modular flange 152 with the first modular flange 121 of the second lamp fixture 120.

The power supply 151 may be electrically connected to the first, second, and third lamp fixtures 110, 120, 130 via the respective first and second connectors 112, 122, 132, 115, 127, 137. Thus, the power supply 151 may provide power to the lamps 113, 124, 134.

The modular emitter system 100 may include a cover (not shown). The cover may be a cap which slides over the second connector 137 of the third lamp fixture 130. The cover may be a housing with a flange. UL requires a tool for removal. The cover may attach to the second connector 137 via a fastener, a snap-fit, as a friction fit, or other method. The cover may attach to the second modular flange 135 of the third lamp fixture 130. The cover may protect the second connector 137 from coming in electrical contact with a person or any stray device. By covering the second connector 137, arcing, electric shock, and potential fire may be avoided.

The modular emitter system 100 may include many lamp fixtures 110. Because the lamp fixtures are strong and rigid, several lamp fixtures may be sequentially mounted to and receive substantial mechanical support from each other via the modular flanges.

Although exemplary embodiments of the present invention have been shown and described, it will be apparent to those having ordinary skill in the art that a number of changes, modifications, or alterations to the invention as described herein may be made, none of which depart from It is claimed:

1. A germicidal system comprising:
   a first, a second, and a third lamp fixture, each lamp fixture comprising
   a housing including a first end and a second end,
   a lamp disposed exterior to the housing and receiving mechanical support from the housing,
   a first mounting flange extending from the housing beyond the first end in a general direction in which the first end faces,
   a second mounting flange extending from the housing beyond the second end in a general direction in which the second end faces,
   a first modular flange extending from the housing beyond the first end in a general direction in which the first end faces,
   a second modular flange extending from the housing beyond the second end in a general direction in which the second end faces,
   a first connector at least partially disposed within an opening of the first end, and
   a second connector at least partially disposed within an opening of the second connector,
   wherein the first connector, second connector and lamp are electrically connected
   the first modular flange of the first lamp fixture attached to the second modular flange of the second lamp fixture,
   the second modular flange of the first lamp fixture attached to the first modular flange of the third lamp fixture,
   the first connector of the first lamp fixture electrically connected to the second connector of the second lamp fixture
   the second connector of the first lamp fixture electrically connected to the first connector of the third lamp fixture
   the first and second mounting flanges of the second lamp fixture and the first and second mounting flanges of the third lamp fixture attached to a fixed surface via attaching means.

2. The germicidal system of claim 1, wherein
   the first flange of the first lamp fixture receives substantial mechanical support solely from the second flange of the second lamp fixture
   the second flange of the first lamp fixture receives substantial mechanical support solely from the first flange of the third lamp fixture.

3. The germicidal system of claim 1, wherein
   the first flange of the first lamp fixture receives principal mechanical support from the second flange of the second lamp fixture
   the second flange of the first lamp fixture receives principal mechanical support from the first flange of the third lamp fixture.

4. The germicidal system of claim 1, further comprising:
   a junction box comprising a modular flange and a connector,
   the modular flange attached to and receiving substantial mechanical support from the second modular flange of the third lamp fixture
   the connector electrically connected to the second connector of the third lamp fixture
   the junction box outputting electric power via the connector.

5. The germicidal system of claim 1, wherein the lamp is an electric discharge lamp.

6. The germicidal system of claim 1, wherein the lamp emits ultraviolet-C radiation.

7. The germicidal system of claim 1, wherein the first, second, and third lamp fixtures are modular fixtures.

8. The germicidal system of claim 1, wherein the first, second, and third lamp fixtures each have a length of less than or equal to 48".

9. The germicidal system of claim 1, wherein the first flange of the first lamp fixture is attached to the second flange of the second lamp fixture and the second flange of the first lamp fixture is attached to the first flange of the third lamp fixture via an attachment selected from the group comprising a snap-fit, a friction fit, a twist lock, and a fastener.

10. The germicidal system of claim 1, further comprising
    a junction box comprising a modular flange and a connector,
    the modular flange attached to and receiving principal mechanical support from the second modular flange of the third lamp fixture
    the connector electrically connected to the second connector of the third lamp fixture
    the junction box providing electric power to the third lamp fixture
    wherein the lamp emits ultraviolet-C radiation
    wherein the first, second, and third lamp fixtures are modular fixtures
    wherein the first, second, and third lamp fixtures each have a length of less than or equal to 48"
    wherein the first modular flange of the first lamp fixture is attached to the second modular flange of the second lamp fixture and the second modular flange of the first lamp fixture is attached to the first modular flange of the third lamp fixture via an attachment selected from the group comprising a snap-fit, a friction fit, a twist lock, and a fastener
    wherein the first modular flange of the first lamp fixture receives principal mechanical support from the second modular flange of the second lamp fixture
    wherein the second modular flange of the first lamp fixture receives principal mechanical support from the first modular flange of the third lamp fixture.

11. An HVAC system comprising the apparatus of claim 10.

12. An electric discharge lamp fixture comprising:
    a housing having a first end and a second end,
    a lamp disposed exterior to the housing and receiving mechanical support from the housing,
    a first mounting flange extending beyond the first end in a general direction which the first end faces,
    a second mounting flange extending beyond the second end in a general direction which the second end faces,
    a first modular flange extending from the housing beyond the first end in a general direction in which the first end faces,
    a second modular flange extending from the housing beyond the second end in a general direction in which the second end faces,
    a first connector at least partially disposed within an opening of the first end, and
    a second connector at least partially disposed within an opening of the second connector,
    wherein the first connector, second connector and lamp are electrically connected, and wherein the first and second modular flanges and the first and second connectors are disposed such that the first modular flange is connectable with the second modular flange of an identical electric discharge lamp fixture when the first connector is mated with the second connector of the identical electric discharge lamp fixture.

13. The apparatus of claim 12, wherein the electric discharge lamp fixture is adapted to receive principal mechanical support solely from at least one other electric discharge lamp fixture.

14. The apparatus of claim 12, wherein the electric discharge lamp fixture is a modular fixture.

15. The apparatus of claim 12, wherein the electric discharge lamp fixture has a length of less than or equal to 48".

16. The apparatus of claim 12, wherein the electric discharge lamp fixture is adapted to provide principal mechanical support to at least one other electric discharge lamp fixture.

17. A process of assembling a modular germicidal system comprising:
electrically connecting a first electric discharge lamp fixture to a second electric discharge lamp fixture, the second electric discharge lamp fixture attached to a fixed surface by means of first and second mounting flanges, wherein electrically connecting the first electric discharge lamp fixture to the second electric discharge lamp fixture aligns the first electric discharge lamp fixture for attaching to the second electric discharge lamp fixture
attaching the first electric discharge lamp fixture to the second electric discharge lamp fixture by means of a first modular flange on the first electric discharge lamp fixture and a second modular flange on the second electric discharge lamp fixture,
wherein the first electric discharge lamp fixture receives substantial mechanical support from the second electric discharge lamp fixture.

18. A germicidal system comprising:
a plurality of lamp fixtures, each lamp fixture comprising
a housing including a first end and a second end
a lamp disposed exterior to the housing and receiving mechanical support from the housing,
a first mounting flange extending from the housing beyond the first end in a general direction in which the first end faces,
a second mounting flange extending from the housing beyond the second end in a general direction in which the second end faces,
a first modular flange extending from the housing beyond the first end in a general direction in which the first end faces,
a second modular flange extending from the housing beyond the second end in a general direction in which the second end faces,
a first connector at least partially disposed within an opening of the first end, and
a second connector at least partially disposed within an opening of the second connector,
wherein the first connector, second connector and lamp are electrically connected
the plurality of lamp fixtures disposed in a linear array including a first lamp fixture, a last lamp fixture, and one or more intermediate lamp fixtures, wherein
the first connector of each intermediate lamp fixture is mated with the second connector of a first adjacent lamp fixture
the first modular flange of each intermediate lamp fixture is attached to the second modular flange of the first adjacent lamp fixture
the second connector of each intermediate lamp fixture is mated with the first connector of a second adjacent lamp fixture
the second modular flange of each intermediate lamp fixture is attached to the first modular flange of the second adjacent lamp fixture
wherein at least the first lamp fixture and the last lamp fixture are attached to a fixed surface by means of the respective first and second mounting flanges.

19. The germicidal system of claim 18, wherein
at least one of the intermediate lamp fixtures receives substantial mechanical support solely from the modular flanges of the lamp fixtures adjacent to the at least one intermediate lamp fixtures.

20. The germicidal system of claim 18, further comprising:
a junction box comprising a modular flange and a connector,
the modular flange attached to and receiving substantial mechanical support from the second modular flange of the last lamp fixture
the connector electrically connected to the second connector of the last lamp fixture
the junction box outputting electric power via the connector.

21. The germicidal system of claim 18, wherein the lamp is an electric discharge lamp.

22. The germicidal system of claim 18, wherein the lamp emits ultraviolet-C radiation.

23. The germicidal system of claim 18, wherein the plurality of lamp fixtures are modular fixtures.

24. The germicidal system of claim 18, wherein the plurality of lamp fixtures each have a length of less than or equal to 48".

* * * * *

UNITED STATES PATENT AND TRADEMARK OFFICE
CERTIFICATE OF CORRECTION

PATENT NO. : 7,282,728 B2  Page 1 of 1
APPLICATION NO. : 10/934811
DATED : October 16, 2007
INVENTOR(S) : Culbert

It is certified that error appears in the above-identified patent and that said Letters Patent is hereby corrected as shown below:

Column 5 line 17, replace "houseing" with --housing--

Column 6 line 27, replace "10" with --110--

Signed and Sealed this

Twenty-seventh Day of November, 2007

JON W. DUDAS
*Director of the United States Patent and Trademark Office*